(12) United States Patent
Serlupi-Crescenzi et al.

(10) Patent No.: US 6,369,198 B1
(45) Date of Patent: Apr. 9, 2002

(54) ALLELIC VARIANT OF HUMAN STAT3

(75) Inventors: Ottaviano Serlupi-Crescenzi; Linda Della Pietra, both of Rome (IT)

(73) Assignee: Applied Research Systems ARS Holding N.V., Curacao (NL)

( * ) Notice: Subject to any disclaimer, the term of this patent is extended or adjusted under 35 U.S.C. 154(b) by 0 days.

(21) Appl. No.: 09/526,542

(22) Filed: Mar. 16, 2000

Related U.S. Application Data

(63) Continuation of application No. PCT/EP98/05844, filed on Sep. 15, 1998.

(30) Foreign Application Priority Data

Sep. 16, 1997 (EP) .............................. 97116061
Feb. 18, 1998 (EP) .............................. 98102774

(51) Int. Cl.[7] .................. C07K 14/00; C07K 14/47; G01N 33/53
(52) U.S. Cl. .................. 530/350; 435/7.1; 514/2; 514/8
(58) Field of Search .................. 530/395, 350, 530/358; 514/885, 2, 8; 435/4, 7.1

(56) References Cited

U.S. PATENT DOCUMENTS 5,844,082 A * 12/1998 Kishimoto et al.

FOREIGN PATENT DOCUMENTS

| EP | 0 676 469 | 10/1995 |
|----|-----------|---------|
| WO | 95 08629  | 3/1995  |
| WO | 96 20954  | 7/1996  |

OTHER PUBLICATIONS

Della Peitra et al. Gene 1998 (Jun. 15) vol. 213, pp. 119–124.*
Oxford Dictionary of Biochemistry and Molecular Biology, Oxford University Press, Oxford 1997, pp. 26–27.*
Akira et al., "Molecular Cloning of APRF, a Novel IFN–Stimulated Gene Factor 3 p91–Related Transcription Factor Involved in the gp130–Mediated Signaling Pathway", *Cell*, vol. 77, pp. 63–71, (1994).
AZAM et al., "Interleukin–3 signals through multiple isoforms of Stat5", *The EMBO Journal*, vol. 14, No. 7, pp. 1402–1411, (1995).
Birnboim, "Rapid extraction of high molecular weight RNA from cultured cells and granulocytes for Northern analysis", *Nucleic Acids Res.*, vol. 16, pp. 1487–1497, (1988).
Darnell "STATs and Gene Regulation", *Science*, vol. 277, pp. 1630–1635, (1997).
Gouilleux et al., "Protactin, growth hormone, erythropoietin and granulocyte–macrophage colony stimulating factor induce MGF–Stat5 DNA binding activity" *The EMBO Journal*, vol. 14, No. 9, pp. 2005–2013, (1995).

Gram et al., "In vitro selection and affinity maturation of antibodies from a naïve combinatorial immunoglobulin liberty", *Proc. Natl. Acad. Sci.*, vol. 89, pp. 3576–3580, (1992).
Harroch et al., "Interleukin–6 Signaling via Four Transcription Factors Binding Palindromic Enhancers of Different Genes", *The Journal of Biological Chemistry*, vol. 269, No. 42, pp. 26191–26195, (1994).
Hemmann et al., "Differential Activation of Acute Phase Response Factor/Stat3 and Stat1 via the Cytoplasmic Domain the Interleukin 6 Signal Transducer gp130", *The Journal of Biological Chemistry*, vol. 271, No. 22, pp. 12999–13007, (1996).
Horvath et al., "A STAT protein domain that determines DNA sequence recognition suggests a novel DNA–binding domain", *Gene & Development*, vol. 9, pp. 984–994 (1995).
Iwatsuki et al., "STAT5 Activation Correlates with Erythropoietin Receptor–mediated Erythroid Differentiation of an Erythroleukemia Cell Line", *The Journal of Biological Chemistry*, vol. 272, No. 13, pp. 8149–8152, (1997).
May et al., "Comparative study on the Phosphotyrosine motifs of different cytokine receptors involved in STAT5 activation", *FEBS Letters*, vol. 394, pp. 221–226, (1996).
Minami et al., "STAT3 activation is a critical step in gp 130–mediated terminals differentiation and growth arrest of a myeloid line", *Proc. Natl. Acad. Sci.*, vol. 93, pp. 3963–3966, (1996).
Quelle et al., "Cloning of Murine Stat6 and Human Stat6, Stat Proteins That Are Tyrosine Phosphorylated in Responses to IL–4 and IL–3 but Are Not Required for Mitogenesis", *Molecular and Cellular Biology*, vol. 15, No. 6, pp. 3336–3343, (1995).
Raz et al., Acute Phase Response Factor and additional Members of the Interferon–Stimulated Gene Factor 3 Family Integrate Diverse Signals from Cytokines, Interferons, and Growth Factors, *The Journal of Biological Chemistry*, vol. 269, No. 39, pp. 24391–24395, (1994).
Sasse et al., "Mutational Analysis of Acute–Phase Response Factor/Sata3 Activation and Dimerzation", *Molecular and Cellular Biology*, vol. 17, No. 8, pp. 4677–4686, (1997).
Seidel et al., "Spacing of Palindromic half sites as a determinant of selective STAT (signal transducers and activators of transcription) DNA binding and transcriptional activity", *Proc. Natl. Acad. Sci.*, vol. 92, pp. 3041–3045, (1995).
Shi et al., "The genomic structure and chromosomal localization of the mouse STAT3 gene", *International Immunology*, vol. 8, No. 8, pp. 1205–1211, (1996).
Silva et al., "Characterization and Cloning of Stat5 from IM–9 Cells and Its Activation by Growth Hormone", *Molecular Endocrinology*, vol. 10, pp. 508–518, (1996).
Stahl et al., "Choice of STATs and Other Substrates Specified by Modular Tyrosine–Based Motifs in Cytokine Receptors", *Science*, vol. 267, pp. 1349–1353, (1995).

(List continued on next page.)

Primary Examiner—Phillip Gambel
Assistant Examiner—Jessica H. Roark
(74) Attorney, Agent, or Firm—Browdy and Neimark

(57) ABSTRACT

An allelic variant of the human STAT3 protein and compositions comprising it are disclosed.

2 Claims, 8 Drawing Sheets

OTHER PUBLICATIONS

Stahl et al., "Association and Activation of Jak–Tyk Kinases by CNTF–LIF–OSM–IL–6 β Receptor Components", *Science*, vol. 263, pp. 92–95, (1994).

Tian et al., "Rapid Activation of the STAT3 Transcription Factor by Granulcyte Colony–Stimulating Factor", *Blood*, vol. 84, No. 6, pp. 1760–1764, (1994).

Wegenka et al., "Acute–Phase Response Factor, a Nuclear Factor Binding to Acute–Phase Response Elements, Is Rapidly Activated by Interleukin–6 at the Posttranslational Level", *Molecular and Cellular Biology*, vol. 13, pp. 276–288, (1993).

Wegenka et al. "The Interleukin–6–Activated Acute–Phase Response Factor Is Antigenically and Functionally Related to Members of the Signal Transducer and Activator of Transcription (STAT) Family", *Molecular and Cellular Biology*, vol. 14, No. 5, pp. 3186–3196, (1994).

Yamanaka et al., "Differentiation and growth arrest signals are generated through the cytoplasmic region of gp130 that is essebtial for Stat3 activation", *The EMBO Journal*, vol. 15, No. 7, pp. 1557–1565, (1996).

Zhang et al., "STAT3 Participates in Transcriptional Activation of Gene C–reactive Protein Gene by Interleukin–6", *The Journal of Biological Chemistry*, vol. 271, No. 16, pp. 9503–9509, (1996).

Zhong et al., "Stat3: A STAT Family Member Activated by Tyrosine Phosphorylation in Response to Epidermal Growth Factor and Interleukin–6", *Science*, vol. 264, pp. 95–98, (1994).

Kaptein et al., "Dominant Negative Stat3 Mutant Inhibits Interleukin–6–induced Jak–STAT Signal Transduction", *The Journal of Biological Chemistry*, vol. 271, No. 11, pp. 5961–5961, (1996).

Caldenhoven et al., "STAT3β, a Splice Variant of Transcription Factor STAT3, Is a Dominant Negative Regulator of Transcription", *The Journal of Biological Chemistry*, vol. 271, No. 21, pp. 13221–13227, (1996).

Ripperger et al., "Transcription Factors Stat3 and Stat5b are Present in Rat Liver Nuclei Late in an Acute Phase Response and Bind Interleukin–6 Response Elements", *The Journal of biological Chemistry*, vol. 270, No. 50, pp. 29998,30006, (1995).

Wen et al., "Maximal Activation of Transcription by Stat1 and Stat3 Required Both Tyrosine and Serine Phosphorylation", *Cell*, vol. 82, pp. 241–250, (1995).

Wang et al., "Naturally Occuring Dominant Negative Variants of Stat5", *Molecular and Cellular Biology*, vol. 16, No. 11, pp. 6141–6148, (1996).

\* cited by examiner

```
  1 ATGGCCCAAT GGAATCAGCT ACAGCAGCTT GACACACGGT ACCTGGAGCA    50
    GCTCCATTGG GAAGCTGTCA CTGTAGAGCT GATGGAGCTG CGGCAGTTTC   100
    TGGCCCCTTG GATTGAGAGT CAAGATTGGG CATATGCGGC CAGCAAAGAA   150
    TCACATGCCA CTTTGGTGTT TCATAATCTC CTGGGAGAGA TTGACCAGCA   200
    GTATAGCCGC TTCCTGCAAG AGTCGAATGT TCTCTATCAG CACAATCTAC   250
    GAAGAATCAA GCAGTTTCTT CAGAGCAGGT ATCTTGAGAA GCCAATGGAG   300
    ATTGCCCGGA TTGTGGCCCG GTGCCTGTGG AAGAATCAC  GCCTTCTACA   350
    GACTGCAGCC ACTGCGGCCC AGCAAGGGGG CCAGGCCAAC CACCCCACAG   400
    CAGCCGTGGT GACGGAGAAG CAGCAGATGC TGGAGCAGCA CCTTCAGGAT   450
    GTCCGGAAGA GAGTGCAGGA TCTAGAACAG AAAATGAAAG TGGTAGAGAA   500
    TCTCCAGGAT GACTTTGATT TCAACTATAA AACCCTCAAG AGTCAAGGAG   550
    ACATGCAAGA TCTGAATGGA AACAACCAGT CAGTGACCAG GCAGAAGATG   600
    CAGCAGCTGG AACAGATGCT CACTGCGCTG ACCAGATGC  GGAGAAGCAT   650
    CGTGAGTGAG CTGGCGGGGC TTTTGTCAGC GATGGAGTAC GTGCAGAAAA   700
    CTCTCACGGA CGAGGAGCTG GCTGACTGGA AGAGGCGGCA ACAGATTGCC   750
    TGCATTGGAG GCCCGCCCAA CATCTGCCTA GATCGGCTAG AAAACTGGAT   800
    AACGTCATTA GCAGAATCTC AACTTCAGAC CCGTCAACAA ATTAAGAAAC   850
    TGGAGGAGTT GCAGCAAAAA GTTTCCTACA AAGGGACCC  CATTGTACAG   900
    CACCGGCCGA TGCTGGAGGA GAGAATCGTG GAGCTGTTTA GAAACTTAAT   950
    GAAAAGTGCC TTTGTGGTGG AGCGGCAGCC CTGCATGCCC ATGCATCCTG  1000
    ACCGGCCCCT CGTCATCAAG ACCGGCGTCC AGTTCACTAC TAAAGTCAGG  1050
    TTGCTGGTCA AATTCCCTGA GTTGAATTAT CAGCTTAAAA TTAAAGTGTG  1100
    CATTGACAAA GACTCTGGGG ACGTTGCAGC TCTCAGAGGA TCCCGGAAAT  1150
    TTAACATTCT GGGCACAAAC ACAAAAGTGA TGAACATGGA AGAATCCAAC  1200
    AACGGCAGCC TCTCTGCAGA ATTCAAACAC TTGACCCTGA GGGAGCAGAG  1250
    ATGTGGGAAT GGGGGCCGAG CCAATTGTGA TGCTTCCCTG ATTGTGACTG  1300
    AGGAGCTGCA CCTGATCACC TTTGAGACCG AGGTGTATCA CCAAGGCCTC  1350
    AAGATTGACC TAGAGACCCA CTCCTTGCCA GTTGTGGTGA TCTCCAACAT  1400
    CTGTCAGATG CCAAATGCCT GGGCGTCCAT CCTGTGGTAC AACATGCTGA  1450
    CCAACAATCC CAAGAATGTA AACTTTTTTA CCAAGCCCCC AATTGGAACC  1500
    TGGGATCAAG TGGCCGAGGT CCTGAGCTGG CAGTTCTCCT CCACCACCAA  1550
    GCGAGGACTG AGCATCGAGC AGCTGACTAC ACTGGCAGAG AAACTCTTGG  1600
    GACCTGGTGT GAATTATTCA GGGTGTCAGA TCACATGGGC TAAATTTTGC  1650
    AAAGAAAACA TGGCTGGCAA GGGCTTCTCC TTCTGGGTCT GGCTAGACAA  1700
    TATCATCGAC CTTGTGAAAA AGTACATCCT GGCCCTTTGG AACGAAGGGT  1750
    ACATCATGGG CTTTATCAGT AAGGAGCGGG AGCGGGCCAT CTTGAGCACT  1800
```

FIGURE 2B

```
AGGCGTCACT TTCACTTGGG TGGAGAAGGA CATCAGCGGT AAGACCCAGA      1900
TCCAGTCCGT GGAACCATAC ACAAAGCAGC AGCTGAACAA CATGTCATTT      1950
GCTGAAATCA TCATGGGCTA TAAGATCATG GATGCTACCA ATATCCTGGT      2000
GTCTCCACTG GTCTATCTCT ATCCTGACAT TCCCAAGGAG GAGGCATTCG      2050
GAAAGTATTG TCGGCCAGAG AGCCAGGAGC ATCCTGAAGC TGACCCAGGT      2100
AGCGCTGCCC CATACCTGAA GACCAAGTTT ATCTGTGTGA CACCAACGAC      2150
CTGCAGCAAT ACCATTGACC TGCCGATGTC CCCCCGCACT TTAGATTCAT      2200
TGATGCAGTT TGGAAATAAT GGTGAAGGTG CTGAACCCTC AGCAGGAGGG      2250
CAGTTTGAGT CCCTCACCTT TGACATGGAG TTGACCTCGG AGTGCGCTAC      2300
CTCCCCCATG TGAGGAGCTG AGAACGGAAG CTGCAGAAAG ATAC            2344
```

FIGURE 2C

SEQUENCE LISTING

<160> NUMBER OF SEQ ID NOS: 19

<210> SEQ ID NO 1
<211> LENGTH: 2344
<212> TYPE: DNA
<213> ORGANISM: Human
<220> FEATURE:
<221> NAME/KEY: CDS
<222> LOCATION: (1)..(2310)

<400> SEQUENCE: 1

| | | | | | | | | | | | | | | | | |
|---|---|---|---|---|---|---|---|---|---|---|---|---|---|---|---|---|
| atg | gcc | caa | tgg | aat | cag | cta | cag | cag | ctt | gac | aca | cgg | tac | ctg | gag | 48 |
| Met | Ala | Gln | Trp | Asn | Gln | Leu | Gln | Gln | Leu | Asp | Thr | Arg | Tyr | Leu | Glu | |
| 1 | | | | 5 | | | | | 10 | | | | | 15 | | |
| cag | ctc | cat | cag | ctc | tac | agt | gac | agc | ttc | cca | atg | gag | ctg | cgg | cag | 96 |
| Gln | Leu | His | Gln | Leu | Tyr | Ser | Asp | Ser | Phe | Pro | Met | Glu | Leu | Arg | Gln | |
| | | | 20 | | | | | 25 | | | | | 30 | | | |
| ttt | ctg | gcc | cct | tgg | att | gag | agt | caa | gat | tgg | gca | tat | gcg | gcc | agc | 144 |
| Phe | Leu | Ala | Pro | Trp | Ile | Glu | Ser | Gln | Asp | Trp | Ala | Tyr | Ala | Ala | Ser | |
| | | | 35 | | | | | 40 | | | | | 45 | | | |
| aaa | gaa | tca | cat | gcc | act | ttg | gtg | ttt | cat | aat | ctc | ctg | gga | gag | att | 192 |
| Lys | Glu | Ser | His | Ala | Thr | Leu | Val | Phe | His | Asn | Leu | Leu | Gly | Glu | Ile | |
| | 50 | | | | | 55 | | | | | 60 | | | | | |
| gac | cag | cag | tat | agc | cgc | ttc | ctg | caa | gag | tcg | aat | gtt | ctc | tat | cag | 240 |
| Asp | Gln | Gln | Tyr | Ser | Arg | Phe | Leu | Gln | Glu | Ser | Asn | Val | Leu | Tyr | Gln | |
| 65 | | | | | 70 | | | | | 75 | | | | | 80 | |
| cac | aat | cta | cga | aga | atc | aag | cag | ttt | ctt | cag | agc | agg | tat | ctt | gag | 288 |
| His | Asn | Leu | Arg | Arg | Ile | Lys | Gln | Phe | Leu | Gln | Ser | Arg | Tyr | Leu | Glu | |
| | | | | 85 | | | | | 90 | | | | | 95 | | |
| aag | cca | atg | gag | att | gcc | cgg | att | gtg | gcc | cgg | tgc | ctg | tgg | gaa | gaa | 336 |
| Lys | Pro | Met | Glu | Ile | Ala | Arg | Ile | Val | Ala | Arg | Cys | Leu | Trp | Glu | Glu | |
| | | | 100 | | | | | 105 | | | | | 110 | | | |
| tca | cgc | ctt | cta | cag | act | gca | gcc | act | gcg | gcc | cag | caa | ggg | ggc | cag | 384 |
| Ser | Arg | Leu | Leu | Gln | Thr | Ala | Ala | Thr | Ala | Ala | Gln | Gln | Gly | Gly | Gln | |
| | | 115 | | | | | 120 | | | | | 125 | | | | |
| gcc | aac | cac | ccc | aca | gca | gcc | gtg | gtg | acg | gag | aag | cag | cag | atg | ctg | 432 |
| Ala | Asn | His | Pro | Thr | Ala | Ala | Val | Val | Thr | Glu | Lys | Gln | Gln | Met | Leu | |
| | 130 | | | | | 135 | | | | | 140 | | | | | |
| gag | cag | cac | ctt | cag | gat | gtc | cgg | aag | aga | gtg | cag | gat | cta | gaa | cag | 480 |
| Glu | Gln | His | Leu | Gln | Asp | Val | Arg | Lys | Arg | Val | Gln | Asp | Leu | Glu | Gln | |
| 145 | | | | | 150 | | | | | 155 | | | | | 160 | |
| aaa | atg | aaa | gtg | gta | gag | aat | ctc | cag | gat | gac | ttt | gat | ttc | aac | tat | 528 |
| Lys | Met | Lys | Val | Val | Glu | Asn | Leu | Gln | Asp | Asp | Phe | Asp | Phe | Asn | Tyr | |
| | | | | 165 | | | | | 170 | | | | | 175 | | |
| aaa | acc | ctc | aag | agt | caa | gga | gac | atg | caa | gat | ctg | aat | gga | aac | aac | 576 |
| Lys | Thr | Leu | Lys | Ser | Gln | Gly | Asp | Met | Gln | Asp | Leu | Asn | Gly | Asn | Asn | |
| | | | 180 | | | | | 185 | | | | | 190 | | | |
| cag | tca | gtg | acc | agg | cag | aag | atg | cag | cag | ctg | gaa | cag | atg | ctc | act | 624 |
| Gln | Ser | Val | Thr | Arg | Gln | Lys | Met | Gln | Gln | Leu | Glu | Gln | Met | Leu | Thr | |
| | | 195 | | | | | 200 | | | | | 205 | | | | |
| gcg | ctg | gac | cag | atg | cgg | aga | agc | atc | gtg | agt | gag | ctg | gcg | ggg | ctt | 672 |
| Ala | Leu | Asp | Gln | Met | Arg | Arg | Ser | Ile | Val | Ser | Glu | Leu | Ala | Gly | Leu | |

-continued

|     | 210 | | | | 215 | | | | 220 | | | | |     |
|-----|-----|-----|-----|-----|-----|-----|-----|-----|-----|-----|-----|-----|-----|-----|

```
ttg tca gcg atg gag tac gtg cag aaa act ctc acg gac gag gag ctg      720
Leu Ser Ala Met Glu Tyr Val Gln Lys Thr Leu Thr Asp Glu Glu Leu
225             230                 235                 240 gct gac tgg aag agg cgg caa cag att gcc tgc att gga ggc ccg ccc      768
Ala Asp Trp Lys Arg Arg Gln Gln Ile Ala Cys Ile Gly Gly Pro Pro
                245                 250                 255 aac atc tgc cta gat cgg cta gaa aac tgg ata acg tca tta gca gaa      816
Asn Ile Cys Leu Asp Arg Leu Glu Asn Trp Ile Thr Ser Leu Ala Glu
            260                 265                 270 tct caa ctt cag acc cgt caa caa att aag aaa ctg gag gag ttg cag      864
Ser Gln Leu Gln Thr Arg Gln Gln Ile Lys Lys Leu Glu Glu Leu Gln
        275                 280                 285 caa aaa gtt tcc tac aaa ggg gac ccc att gta cag cac cgg ccg atg      912
Gln Lys Val Ser Tyr Lys Gly Asp Pro Ile Val Gln His Arg Pro Met
    290                 295                 300 ctg gag gag aga atc gtg gag ctg ttt aga aac tta atg aaa agt gcc      960
Leu Glu Glu Arg Ile Val Glu Leu Phe Arg Asn Leu Met Lys Ser Ala
305                 310                 315                 320 ttt gtg gtg gag cgg cag ccc tgc atg ccc atg cat cct gac cgg ccc     1008
Phe Val Val Glu Arg Gln Pro Cys Met Pro Met His Pro Asp Arg Pro
                325                 330                 335 ctc gtc atc aag acc ggc gtc cag ttc act act aaa gtc agg ttg ctg     1056
Leu Val Ile Lys Thr Gly Val Gln Phe Thr Thr Lys Val Arg Leu Leu
            340                 345                 350 gtc aaa ttc cct gag ttg aat tat cag ctt aaa att aaa gtg tgc att     1104
Val Lys Phe Pro Glu Leu Asn Tyr Gln Leu Lys Ile Lys Val Cys Ile
        355                 360                 365 gac aaa gac tct ggg gac gtt gca gct ctc aga gga tcc cgg aaa ttt     1152
Asp Lys Asp Ser Gly Asp Val Ala Ala Leu Arg Gly Ser Arg Lys Phe
    370                 375                 380 aac att ctg ggc aca aac aca aaa gtg atg aac atg gaa gaa tcc aac     1200
Asn Ile Leu Gly Thr Asn Thr Lys Val Met Asn Met Glu Glu Ser Asn
385                 390                 395                 400 aac ggc agc ctc tct gca gaa ttc aaa cac ttg acc ctg agg gag cag     1248
Asn Gly Ser Leu Ser Ala Glu Phe Lys His Leu Thr Leu Arg Glu Gln
                405                 410                 415 aga tgt ggg aat ggg ggc cga gcc aat tgt gat gct tcc ctg att gtg     1296
Arg Cys Gly Asn Gly Gly Arg Ala Asn Cys Asp Ala Ser Leu Ile Val
            420                 425                 430 act gag gag ctg cac ctg atc acc ttt gag acc gag gtg tat cac caa     1344
Thr Glu Glu Leu His Leu Ile Thr Phe Glu Thr Glu Val Tyr His Gln
        435                 440                 445 ggc ctc aag att gac cta gag acc cac tcc ttg cca gtt gtg gtg atc     1392
Gly Leu Lys Ile Asp Leu Glu Thr His Ser Leu Pro Val Val Val Ile
    450                 455                 460 tcc aac atc tgt cag atg cca aat gcc tgg gcg tcc atc ctg tgg tac     1440
Ser Asn Ile Cys Gln Met Pro Asn Ala Trp Ala Ser Ile Leu Trp Tyr
465                 470                 475                 480 aac atg ctg acc aac aat ccc aag aat gta aac ttt ttt acc aag ccc     1488
Asn Met Leu Thr Asn Asn Pro Lys Asn Val Asn Phe Phe Thr Lys Pro
                485                 490                 495 cca att gga acc tgg gat caa gtg gcc gag gtc ctg agc tgg cag ttc     1536
Pro Ile Gly Thr Trp Asp Gln Val Ala Glu Val Leu Ser Trp Gln Phe
            500                 505                 510 tcc tcc acc acc aag cga gga ctg agc atc gag cag ctg act aca ctg     1584
Ser Ser Thr Thr Lys Arg Gly Leu Ser Ile Glu Gln Leu Thr Thr Leu
        515                 520                 525 gca gag aaa ctc ttg gga cct ggt gtg aat tat tca ggg tgt cag atc     1632
```

-continued

```
            Ala Glu Lys Leu Leu Gly Pro Gly Val Asn Tyr Ser Gly Cys Gln Ile
                530                 535                 540 aca tgg gct aaa ttt tgc aaa gaa aac atg gct ggc aag ggc ttc tcc         1680
Thr Trp Ala Lys Phe Cys Lys Glu Asn Met Ala Gly Lys Gly Phe Ser
545                 550                 555                 560 ttc tgg gtc tgg cta gac aat atc atc gac ctt gtg aaa aag tac atc         1728
Phe Trp Val Trp Leu Asp Asn Ile Ile Asp Leu Val Lys Lys Tyr Ile
                565                 570                 575 ctg gcc ctt tgg aac gaa ggg tac atc atg ggc ttt atc agt aag gag         1776
Leu Ala Leu Trp Asn Glu Gly Tyr Ile Met Gly Phe Ile Ser Lys Glu
            580                 585                 590 cgg gag cgg gcc atc ttg agc act aag cct cca ggc acc ttc ctg cta         1824
Arg Glu Arg Ala Ile Leu Ser Thr Lys Pro Pro Gly Thr Phe Leu Leu
        595                 600                 605 aga ttc agt gaa agc agc aaa gaa gga ggc gtc act ttc act tgg gtg         1872
Arg Phe Ser Glu Ser Ser Lys Glu Gly Gly Val Thr Phe Thr Trp Val
    610                 615                 620 gag aag gac atc agc ggt aag acc cag atc cag tcc gtg gaa cca tac         1920
Glu Lys Asp Ile Ser Gly Lys Thr Gln Ile Gln Ser Val Glu Pro Tyr
625                 630                 635                 640 aca aag cag cag ctg aac aac atg tca ttt gct gaa atc atc atg ggc         1968
Thr Lys Gln Gln Leu Asn Asn Met Ser Phe Ala Glu Ile Ile Met Gly
                645                 650                 655 tat aag atc atg gat gct acc aat atc ctg gtg tct cca ctg gtc tat         2016
Tyr Lys Ile Met Asp Ala Thr Asn Ile Leu Val Ser Pro Leu Val Tyr
                660                 665                 670 ctc tat cct gac att ccc aag gag gag gca ttc gga aag tat tgt cgg         2064
Leu Tyr Pro Asp Ile Pro Lys Glu Glu Ala Phe Gly Lys Tyr Cys Arg
            675                 680                 685 cca gag agc cag gag cat cct gaa gct gac cca ggt agc gct gcc cca         2112
Pro Glu Ser Gln Glu His Pro Glu Ala Asp Pro Gly Ser Ala Ala Pro
        690                 695                 700 tac ctg aag acc aag ttt atc tgt gtg aca cca acg acc tgc agc aat         2160
Tyr Leu Lys Thr Lys Phe Ile Cys Val Thr Pro Thr Thr Cys Ser Asn
705                 710                 715                 720 acc att gac ctg ccg atg tcc ccc cgc act tta gat tca ttg atg cag         2208
Thr Ile Asp Leu Pro Met Ser Pro Arg Thr Leu Asp Ser Leu Met Gln
                725                 730                 735 ttt gga aat aat ggt gaa ggt gct gaa ccc tca gca gga ggg cag ttt         2256
Phe Gly Asn Asn Gly Glu Gly Ala Glu Pro Ser Ala Gly Gly Gln Phe
                740                 745                 750 gag tcc ctc acc ttt gac atg gag ttg acc tcg gag tgc gct acc tcc         2304
Glu Ser Leu Thr Phe Asp Met Glu Leu Thr Ser Glu Cys Ala Thr Ser
            755                 760                 765 ccc atg tgaggagctg agaacggaag ctgcagaaag atac                           2344
Pro Met
    770

<210> SEQ ID NO 2
<211> LENGTH: 770
<212> TYPE: PRT
<213> ORGANISM: Human

<400> SEQUENCE: 2

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45
```

-continued

```
Lys Glu Ser His Ala Thr Leu Val Phe His Asn Leu Leu Gly Glu Ile
 50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
                 85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460
```

-continued

```
Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
            485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met
    770

<210> SEQ ID NO 3
<211> LENGTH: 424
<212> TYPE: DNA
<213> ORGANISM: Human
<220> FEATURE:
<221> NAME/KEY: CDS
<222> LOCATION: (2)..(424)
<221> NAME/KEY: misc_feature
<222> LOCATION: (2)..(424)
<223> OTHER INFORMATION: note: "SH2 domain of the published hSTAT3
      sequence (Akira et al.)

<400> SEQUENCE: 3 c tgg cta gac aat atc atc gac ctt gtg aaa aag tat atc ttg gcc ctt      49
  Trp Leu Asp Asn Ile Ile Asp Leu Val Lys Lys Tyr Ile Leu Ala Leu
  1               5                  10                  15
```

-continued

| | |
|---|---|
| tgg aat gaa ggg tac atc atg ggt ttc atc agc aag gag cgg gag cgg<br>Trp Asn Glu Gly Tyr Ile Met Gly Phe Ile Ser Lys Glu Arg Glu Arg<br>20 25 30 | 97 |
| gcc atc ttg agc act aag ccc cca ggc acc ttc ctg ctg cgc ttc agt<br>Ala Ile Leu Ser Thr Lys Pro Pro Gly Thr Phe Leu Leu Arg Phe Ser<br>35 40 45 | 145 |
| gaa agc agc aaa gaa gga ggc gtc act ttc act tgg gtg gag aag gac<br>Glu Ser Ser Lys Glu Gly Gly Val Thr Phe Thr Trp Val Glu Lys Asp<br>50 55 60 | 193 |
| atc agc ggt aag acc cag atc cag tcc gtg gaa cca tac aca aag cag<br>Ile Ser Gly Lys Thr Gln Ile Gln Ser Val Glu Pro Tyr Thr Lys Gln<br>65 70 75 80 | 241 |
| cag ctg aac aac atg tca ttt gct gaa atc atc atg ggc tat aag atc<br>Gln Leu Asn Asn Met Ser Phe Ala Glu Ile Ile Met Gly Tyr Lys Ile<br>85 90 95 | 289 |
| atg gat gct acc aat atc ctg ttg tct cca ctt gtc tat ctc tat cct<br>Met Asp Ala Thr Asn Ile Leu Leu Ser Pro Leu Val Tyr Leu Tyr Pro<br>100 105 110 | 337 |
| gac att ccc aag gag gag gca ttc ggg aag tat tgt cgg cca gag agc<br>Asp Ile Pro Lys Glu Glu Ala Phe Gly Lys Tyr Cys Arg Pro Glu Ser<br>115 120 125 | 385 |
| cag gag cat cct gaa gct gac cca ggt agc gct gcc cca<br>Gln Glu His Pro Glu Ala Asp Pro Gly Ser Ala Ala Pro<br>130 135 140 | 424 |

<210> SEQ ID NO 4
<211> LENGTH: 141
<212> TYPE: PRT
<213> ORGANISM: Human
<220> FEATURE:
<221> NAME/KEY: misc_feature
<222> LOCATION: (2)..(424)
<223> OTHER INFORMATION: note: "SH2 domain of the published hSTAT3
      sequence (Akira et al.)

<400> SEQUENCE: 4

Trp Leu Asp Asn Ile Ile Asp Leu Val Lys Lys Tyr Ile Leu Ala Leu
1               5                   10                  15

Trp Asn Glu Gly Tyr Ile Met Gly Phe Ile Ser Lys Glu Arg Glu Arg
                20                  25                  30

Ala Ile Leu Ser Thr Lys Pro Pro Gly Thr Phe Leu Leu Arg Phe Ser
            35                  40                  45

Glu Ser Ser Lys Glu Gly Gly Val Thr Phe Thr Trp Val Glu Lys Asp
        50                  55                  60

Ile Ser Gly Lys Thr Gln Ile Gln Ser Val Glu Pro Tyr Thr Lys Gln
65                  70                  75                  80

Gln Leu Asn Asn Met Ser Phe Ala Glu Ile Ile Met Gly Tyr Lys Ile
                85                  90                  95

Met Asp Ala Thr Asn Ile Leu Leu Ser Pro Leu Val Tyr Leu Tyr Pro
            100                 105                 110

Asp Ile Pro Lys Glu Glu Ala Phe Gly Lys Tyr Cys Arg Pro Glu Ser
        115                 120                 125

Gln Glu His Pro Glu Ala Asp Pro Gly Ser Ala Ala Pro
    130                 135                 140

<210> SEQ ID NO 5
<211> LENGTH: 424
<212> TYPE: DNA
<213> ORGANISM: Mouse
<220> FEATURE:
<221> NAME/KEY: CDS

```
<222> LOCATION: (2)..(424)
<221> NAME/KEY: misc_feature
<222> LOCATION: (2)..(424)
<223> OTHER INFORMATION: note: "SH2 domain of murine STAT3"

<400> SEQUENCE: 5 c tgg cta gac aat atc atc gac ctt gtg aaa aag tat atc ttg gcc ctt      49
  Trp Leu Asp Asn Ile Ile Asp Leu Val Lys Lys Tyr Ile Leu Ala Leu
  1               5                   10                  15 tgg aat gaa ggg tac atc atg ggt ttc atc agc aag gag cgg gag cgg         97
Trp Asn Glu Gly Tyr Ile Met Gly Phe Ile Ser Lys Glu Arg Glu Arg
            20                  25                  30 gcc atc cta agc aca aag ccc ccg ggc acc ttc cta ctg cgc ttc agc        145
Ala Ile Leu Ser Thr Lys Pro Pro Gly Thr Phe Leu Leu Arg Phe Ser
        35                  40                  45 gag agc agc aaa gaa gga ggg gtc act ttc act tgg gtg gaa aag gac        193
Glu Ser Ser Lys Glu Gly Gly Val Thr Phe Thr Trp Val Glu Lys Asp
    50                  55                  60 atc agt ggc aag acc cag atc cag tct gta gag cca tac acc aag cag        241
Ile Ser Gly Lys Thr Gln Ile Gln Ser Val Glu Pro Tyr Thr Lys Gln
65                  70                  75                  80 cag ctg aac aac atg tca ttt gct gaa atc atc atg ggc tat aag atc        289
Gln Leu Asn Asn Met Ser Phe Ala Glu Ile Ile Met Gly Tyr Lys Ile
                85                  90                  95 atg gat gcg acc aac atc ctg gtg tct cca ctt gtc tac ctc tac ccc        337
Met Asp Ala Thr Asn Ile Leu Val Ser Pro Leu Val Tyr Leu Tyr Pro
            100                 105                 110 gac att ccc aag gag gag gca ttt gga aag tac tgt agg ccc gag agc        385
Asp Ile Pro Lys Glu Glu Ala Phe Gly Lys Tyr Cys Arg Pro Glu Ser
        115                 120                 125 cag gag cac ccc gaa gcc gac cca ggt agc tct gcc cca                    424
Gln Glu His Pro Glu Ala Asp Pro Gly Ser Ser Ala Pro
    130                 135                 140

<210> SEQ ID NO 6
<211> LENGTH: 141
<212> TYPE: PRT
<213> ORGANISM: Mouse
<220> FEATURE:
<221> NAME/KEY: misc_feature
<222> LOCATION: (2)..(424)
<223> OTHER INFORMATION: note: "SH2 domain of murine STAT3"

<400> SEQUENCE: 6

Trp Leu Asp Asn Ile Ile Asp Leu Val Lys Lys Tyr Ile Leu Ala Leu
1               5                   10                  15

Trp Asn Glu Gly Tyr Ile Met Gly Phe Ile Ser Lys Glu Arg Glu Arg
            20                  25                  30

Ala Ile Leu Ser Thr Lys Pro Pro Gly Thr Phe Leu Leu Arg Phe Ser
        35                  40                  45

Glu Ser Ser Lys Glu Gly Gly Val Thr Phe Thr Trp Val Glu Lys Asp
    50                  55                  60

Ile Ser Gly Lys Thr Gln Ile Gln Ser Val Glu Pro Tyr Thr Lys Gln
65                  70                  75                  80

Gln Leu Asn Asn Met Ser Phe Ala Glu Ile Ile Met Gly Tyr Lys Ile
                85                  90                  95

Met Asp Ala Thr Asn Ile Leu Val Ser Pro Leu Val Tyr Leu Tyr Pro
            100                 105                 110

Asp Ile Pro Lys Glu Glu Ala Phe Gly Lys Tyr Cys Arg Pro Glu Ser
        115                 120                 125
```

-continued

Gln Glu His Pro Glu Ala Asp Pro Gly Ser Ser Ala Pro
    130                 135                 140

<210> SEQ ID NO 7
<211> LENGTH: 47
<212> TYPE: DNA
<213> ORGANISM: Artificial: Probe

<400> SEQUENCE: 7
aacaccatgg cctggctaga caatatcatc gaccttgtga aaaagta          47

<210> SEQ ID NO 8
<211> LENGTH: 39
<212> TYPE: DNA
<213> ORGANISM: Artificial: Probe

<400> SEQUENCE: 8
atatatggat cctggggcag cgctacctgg gtcagcttc                   39

<210> SEQ ID NO 9
<211> LENGTH: 35
<212> TYPE: DNA
<213> ORGANISM: Artificial: Probe

<400> SEQUENCE: 9
tccccggaag cttcacacgc gcagccccgg cttct                       35

<210> SEQ ID NO 10
<211> LENGTH: 30
TYPE: DNA
<213> ORGANISM: Artificial: Probe

<400> SEQUENCE: 10
gttcatcact tttgtgtttg tgcccagaat                             30

<210> SEQ ID NO 11
<211> LENGTH: 30
TYPE: DNA
<213> ORGANISM: Artificial: Probe

<400> SEQUENCE: 11
gacaaagact ctggggacgt tgcagctctc                             30

<210> SEQ ID NO 12
<211> LENGTH: 35
TYPE: DNA
<213> ORGANISM: Artificial: Probe

<400> SEQUENCE: 12
tcagtcctcg agtatctttc tgcagcttcc gttct                       35

<210> SEQ ID NO 13
<211> LENGTH: 22
TYPE: DNA
<213> ORGANISM: Artificial: Probe

<400> SEQUENCE: 13
tgaagggtac atcatgggtt tc                                     22

<210> SEQ ID NO 14
<211> LENGTH: 29
TYPE: DNA
<213> ORGANISM: Artificial: Probe

-continued

```
<400> SEQUENCE: 14
tcaggataga gatagacaag tggagacaa                                         29

<210> SEQ ID NO 15
<211> LENGTH: 27
TYPE: DNA
<213> ORGANISM: Artificial: Probe

<400> SEQUENCE: 15
cctccttctt tgctgctttc actgaag                                           27

<210> SEQ ID NO 16
<211> LENGTH: 22
TYPE: DNA
<213> ORGANISM: Artificial: Probe

<400> SEQUENCE: 16
cgaagggtac atcatgggct tt                                                22

<210> SEQ ID NO 17
<211> LENGTH: 30
TYPE: DNA
<213> ORGANISM: Artificial: Probe

<400> SEQUENCE: 17
cctccttctt tgctgctttc actgaatctt                                        30

<210> SEQ ID NO 18
<211> LENGTH: 33
TYPE: DNA
<213> ORGANISM: Artificial: Probe

<400> SEQUENCE: 18
tgaagggtac atcatgggtt tcatcagtaa gga                                    33

<210> SEQ ID NO 19
<211> LENGTH: 37
TYPE: DNA
<213> ORGANISM: Artificial: Probe

<400> SEQUENCE: 19
tcaggataga gatagacaag tggagacaac aggatat                                37
```

ALLELIC VARIANT OF HUMAN STAT3

CROSS REFERENCE TO RELATED APPLICATION

The present application is continuation of International Application No. PCT/EP98/05844, filed Sep. 15, 1998, the entire contents of which being hereby incorporated herein by reference.

FIELD OF THE INVENTION

The present invention relates to human STAT3 allelic variant, cDNA sequence encoding it, its use in therapy and/or in diagnosis of autoimmune and/or inflammatory diseases, as well as pharmaceutical compositions comprising it.

BACKGROUND OF THE INVENTION

Signal Transducer and Activator of Transcription (STAT) proteins are a new class of intracellular transcription factors which play an essential function in the cellular responses to cytokines (Stahl et al., 1994; Gouilleux et al., 1995; Azam et al., 1995; Tian et al., 1994; May et al., 1996; and Iwatsuki et al., 1997).

Most of these proteins have been well characterized by sequencing, and their structure as well as the mechanism of their actions has been extensively analyzed and well documented (Wegenka et al., 1993; Akira et al., 1994; Wegenka et al., 1994; Quelle et al., 1995 and Silva et al., 1996).

These proteins contains SH2 and SH3 domains as well as phosphorylation site at their carboxy-terminal region (Kapetein et al., 1996; and Herman et al., 1996). After cytokine receptor activation through ligand binding, the intracellular portion of the receptor becomes phosphorylated by an associated kinase of the JAK family.

STAT proteins then bind to the phosphorylated receptor, through their SH2 domain and are in turn phosphorylated by JAKs (Stahl et al., 1995). Phosphorylated STAT proteins then dimerize and translocate to the nucleus, where they are able to recognize specific DNA responsive elements (Seidel et al., 1995; and Harroch et al., 1994).

STAT3 has been identified as an important mediator of the signal imparted by the IL-6 family of cytokines, as well as by EGF and by a number of other interleukins and growth factors.

STAT3 has been shown to play a central role in the upregulation of hepatic acute-phase proteins (Wagenka et al., 1993; and Zhang et al., 1996) in the growth arrest of monocytic cells (Yamanaka et al., 1996; and Minami et al., 1996) as well as in the survival of myleoma cells (Harroch et al., 1994).

DESCRIPTION OF THE INVENTION

During experiments on the analysis of STAT3 interactions, we have amplified by RT-PCR from HepG2 cells a cDNA fragment corresponding to the SH2 domain of human STAT3. We have found by DNA sequencing that the SH2 domain we have isolated shows a divergence of 13 residues over the corresponding sequence of the original published human STAT3 gene (Akira et al., 1994).

In order to determine the nature of this sequence variant, we have designed three pairs of primers with 3' ends corresponding to nucleotide positions at variance between the two human cDNA sequences.

Upon such investigations it resulted that the new variant corresponds to at least the most frequence allele of human STAT3.

Therefore, the main object of this invention is the above-mentioned allelic variant of human STAT3 protein. In particular, the object of the invention is a polypeptide comprising the amino acid sequence of SEQ ID NO: 2, or a functionally equivalent salt, or a functionally equivalent derivative, or an active fraction, or a fusion protein.

The definition "salt" as used herein refers both to salts of the carboxy-groups and to the salts of the amino functions of the compound obtainable through known methods. The salts of the carboxyl-groups comprise inorganic salts as, for example, sodium, potassium, calcium salts and salts with organic bases as those formed with an amine as triethanolamine, arginine or lisine. The salts of the amino groups comprise for example salts with inorganic acids as hydrochloric acid and with organic acids as acetic acid.

The definition "derivative" as herein used refers to derivatives which can be prepared from the functional groups present on the lateral chains of the amino acid moieties or on the terminal N- or C- groups according to known methods and are comprised in the invention when they are pharmaceutically acceptable i.e. when they do not destroy the protein activity or do not impart toxicity to the pharmaceutical compositions containing them. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

As "active fraction" of the protein the present invention refers to any fragment or precursor of the polypeptidic chain of the compound itself, alone or in combination with related molecules or residues bound to it, for example residues of sugars or phosphates, or aggregates of the polypeptide molecule when such fragments or precursors show the same activity of the protein of the invention, as medicament.

The definition "fusion protein" as herein used refers to polypeptides comprising the polypeptide of the invention above specified fused with another protein and having a longer lasting half-life in body fluids. It can for example be fused with another protein such as, for example, an immunoglobulin.

Another object of the invention is the DNA molecule comprising the DNA sequence coding for the allelic variant of the invention, including nucleotide sequences substantially the same.

"Nucleotide sequences substantially the same" includes all other nucleic acid sequences which, by viture of degeneracy of the genetic code, also code for the given amino acid sequences. In particular, the present invention refers to the nucleotide sequence comprising the SEQ ID NO: 1.

The present invention also refers to recombinant DNA molecules which hybridize with the DNA sequence coding for the above-mentioned allelic variant of hSTAT3 and whose nucleotide sequences show at least the same 13 differences in the SH2 domain (with respect to the human STAT3 sequence in Akira et al., 1994), as shown in FIG. 1. The gene can contain, or not, the natural introns and can be obtained for example by extraction from appropriate cells and purification with known methods.

Furthermore, the present invention also includes recombinant DNA molecules which hybridize under stingent conditions with a probe having a nucleotide sequence selected between SEQ ID NO: 16 and SEQ ID NO: 17.

The term "stringent conditions" refers to hybridization and subsequent washing conditions which those of ordinary skill in the art conventionally refer to as "stringent". See Ausubel et al., *Current Protocols in Molecular Biologic supra. Interscience, N.Y.*, pare. 6.3 and 6.4 (1987, 1992), and Sambrook et al., 1989. Without limitation, examples of stingent conditions include washing conditions 12–20° C. below the calculated Tm of the hybrid under study in, e.g. 2×SSC and 0.5% SDS for 5 minutes, 2×SSC and 0.1% SDS for 15 minutes; 0.1×SSC and 0.5% SDS at 37° C. for 30–60 minutes and then a 0.1×SSC and 0.5% SDS at 68° C. for-30–60 minutes. Those of ordinary skill in this art understand that stringency conditions also depend on the length of the DNA sequences, oligonucleotide probes (such as 10–40 bases) or mixed oligonucleotide probes. If mixed probes are used, it is preferable to use tetramethyl ammonium chloride (TMAC) instead of SSC. See *Ausubel*, supra.

The invention also includes expression vectors which comprise the above DNAs, host-cells transformed with such vectors and a process of preparation of such allelic variant of hSTAT3, its active fragments or fusion proteins, through the culture in appropriate culture media of said transformed cells.

The DNA sequence coding for the protein of the invention can be inserted and ligated into a suitable plasmid. Once formed, the expression vector is introduced into a suitable host cell, which then expresses the vector(s) to yield the desired protein.

Expression of any of the recombinant proteins of the invention as mentioned herein can be effected in eukaryotic cells (e.g. yeasts, insect or mammalian cells) or prokaryotic cells, using the appropriate expression vectors. Any method known in the art can be employed.

For example the DNA molecules coding for the proteins obtained by any of the above methods are inserted into appropriately constructed expression vectors by techniques well known in the art (see Sambrook et al., 1989). Double stranded cDNA is linked to plasmid vectors by homopolymeric tailing or by restriction linking involving the use of synthetic DNA linkers or blunt-ended ligation techniques: DNA ligases are used to ligate the DNA molecules and undesirable joining is avoided by treatment with alkaline phosphatase.

In order to be capable of expressing the desired protein, an expression vector should comprise also specific nucleotide sequences containing transcriptional and translational regulatory information linked to the DNA coding the desired protein in such a way as to permit gene expression and production of the protein. First in order for the gene to be transcribed, it must be preceded by a promoter recognizable by RNA polymerase, to which the polymerase binds and thus initiates the transcription process. There are a variety of such promoters in use, which work with different efficiencies (strong and weak promoters).

For eukaryotic hosts, different transcriptional and translational regulatory sequences may be employed, depending on the nature of the host. They may be derived from viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for the protein of the invention is inserted into vector(s), having the operably linked transcriptional and translational regulatory signals, which is capable of integrating the desired gene sequences into the host cell.

The cells which have been stably transformed by the introduced DNA can be selected by also introducing one or more markers which allow for selection of host cells which contain the expression vector. The marker may also provide for phototrophy to a auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

Factors of importance in selecting a particular plasmid or viral vector include: the ease with which recipient cells, that contain the vector may be recognized and selected form those recipient cells which do not contain the vector; the number of copies of the vector which are desired in a particular host; and whether it is desirable to be able to "shuttle" the vector between host cells of different species.

Once the vector(s) or DNA sequence containing the construct(s) has been prepared for expression the DNA construct(s) may be introduced into an appropriate host cell by any of a variety of suitable means: transformation, transfection, conjugation, photoplast fusion, electroporation, calcium phosphate-precipitation, direct microinjection, etc.

Host cells, may be either prokaryotic or eukaryotic. Preferred are eukaryotic hosts, e.g. mammalian cells, such as human, monkey, mouse, and Chinese hamster ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides).

After the introduction of the vector(s), the host cells are grown in a selective medium, which selects for the growth of vector-containing cells. Expression of the cloned gene sequence(s) results in the production of the desired proteins.

Purification of the recombinant proteins is carried out by any one of the methods known for this purpose, i.e. any conventional procedure involving extraction, precipitation, chromatography, electrophoresis, or the like. A further purification procedure that may be used in preference for purifying the protein of the invention is affinity chromatography using monoclonal antibodies which bind the target protein and which are produced and immobilized on a gel matrix contained within a column. Impure preparations containing the recombinant protein are passed through the column. The protein will be bound to the column by the specific antibody while the impurities will pass through. After washing, the protein is eluted from the gel by a change in pH or ionic strength.

As already stated, the protein of the invention is useful in the therapy and/or diagnosis of autoimmune and/or inflammatory diseases. Therefore, in a further aspect, the present invention provides the use of the protein of the invention in the manufacture of a medicament for the treatment of autoimmune diseases and/or inflammatory diseases.

The medicament is preferably presented in the form of a pharmaceutical composition comprising the protein of the invention together with one or more pharmaceutically acceptable carriers and/or excipients. Such pharmaceutical compositions form yet a further aspect of the present invention.

The invention will now be described by means of the following Examples, which should not be construed as in any way limiting the present invention. The Examples will refer to the Figures specified here below.

DESCRIPTION OF THE FIGURES

FIGS. 2A, 2B and 2C report the complete nucleotide sequence of human STAT3 isolated from human HepG2 cells, in particular the coding region.

FIGS 3A and 3C show PCR products amplified with the US1/LS1 pair of primers specific for the original published hSTAT3 sequence, and FIGS. 3B and 3D show PCR products amplified with the US3/LS3 pair of primers specific for the new hSTAT3 sequence variant found in this patent application. The lanes are as follows: M) Molecular size markers. 1) Liver RNA. 2) Spleen RNA. 3) Uterus RNA. 4) Lung RNA. 5) Skin RNA. 6) RNA from cord blood cells. 7) Dermal fibroblasts RNA. 8) Heart RNA with no reverse transcriptase. 9) Heart RNA. 10) Fetal liver RNA with no reverse transcriptase. 11) Fetal liver RNA. 12) Small intestine RNA with no reverse transcriptase. 13) Small intestine RNA. 14) Placental RNA with no reverse transcriptase. 15) Placental RNA.

EXAMPLES

MATERIALS AND METHODS

Materials

HepG2 human hepatoma cell line was from ATCC (Rockville, Md., USA). Total human RNA from heart, liver, fetal liver, small intestine placenta and human genomic DNA were obtained from Clontech (Palo Alto, Calif., USA). Other RNAs used in this patent application were prepared in our laboratory.

Pfu polymerase was from Stratagene (La Jolla, Calif., USA); DNA Tag polymerase was from Advance Biotechnology, Leatherland, UK. DNA Sequencing Kit was from Perkin Elmer (Applied Biosystems Division, Foster City, Calif. USA); SuperScript II reverse transcriptase (200 U/μl) and Trizol Reagent for RNA extraction were from Gibco (Grand Island, N.Y., USA).

Oligonucleotide primers

All primers used in this patent application were designed in our laboratory using the software OLIGO (National Biosciences, Plymouth, Minn., USA), in order to optimize the specificity of PCR amplification of template nucleotide sequences differing by only one or few nucleotides.

All primers were synthesized in our laboratory, with a 392 DNA/RNA Synthesizer from Perkin Elmer (Applied Biosystems Division, Foster City, Calif., USA). A first pair of primers, US0/LS0, was used for the isolation of 424 bp containing the whole SH2 domain of human STAT3 cDNA.

The nucleotide sequences of all the primers used are shown below.

```
Primer US0   5'AAC ACC ATG GCC TGG CTA GAC AAT ATC ATC GAC CTT          SEQ ID NO: 7
             GTG AAA AAG TA 3'
Primer LS0   5'ATA TAT GGA TCC TGG GGC AGC GCT ACC TGG GTC AGC TTC 3'   SEQ ID NO: 8
             TTC 3'
Primer STAU  5'TCC CCG GAA GCT TCA CAC GCG CAG CCC CGG CTT CT 3'        SEQ ID NO: 9
Primer STAL  5'GTT CAT CAC TTT TGT GTT TGT GCC CAG AAT 3'.              SEQ ID NO: 10
```

-continued

| Primer STBU | 5'GAC AAA GAC TCT GGG GAC GTT GCA GCT CTC 3'. | SEQ ID NO: 11 |
| Primer STBL | 5'TCA GTC CTC GAG TAT CTT TCT GCA GCT TCC GTT CT 3' | SEQ ID NO: 12 |
| Primer US1 | 5'TGA AGG GTA CAT CAT GGG TTT C 3' | SEQ ID NO: 13 |
| Primer LS1 | 5'TCA GGA TAG AGA TAG ACA AGT GGA GAC AA 3' | SEQ ID NO: 14 |
| Primer LS2 | 5'CCT CCT TCT TTG CTG CTT TCA CTG AAG 3' | SEQ ID NO: 15 |
| Primer US3 | 5'CGA AGG GTA CAT CAT GGG CTT T 3' | SEQ ID NO: 16 |
| Primer LS3 | 5'CCT CCT TCT TTG CTG CTT TCA CTG AAT CTT 3' | SEQ ID NO: 17 |
| Primer US4 | 5'TGA AGG GTA CAT CAT GGG TTT CAT CAG TAA GGA 3' | SEQ ID NO: 18 |
| Primer LS4 | 5'TCA GGA TAG AGA TAG ACA AGT GGA GAC AAC AGG ATA T 3' T 3' | SEQ ID NO: 19 |

Figure 1:
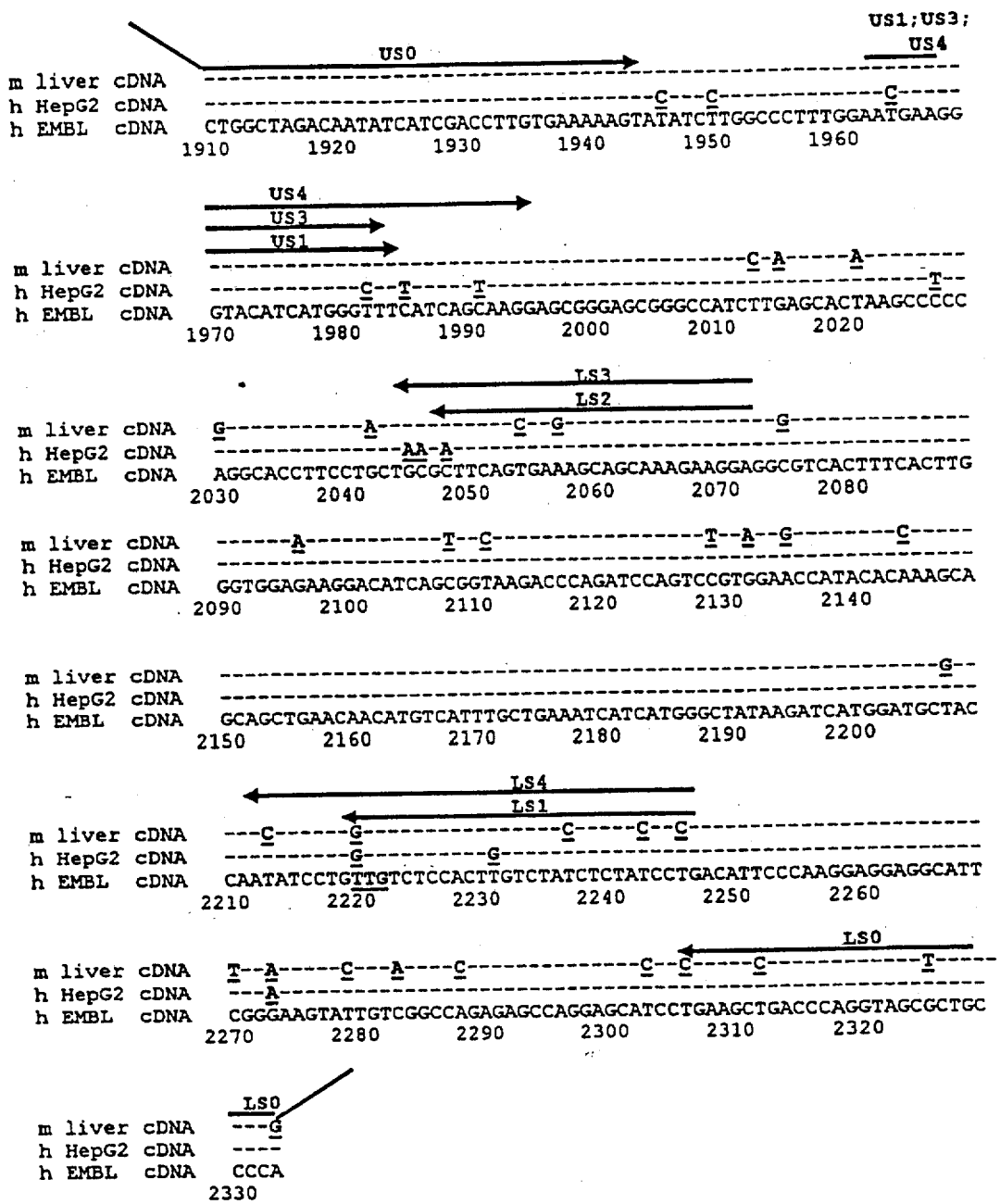
FIG. 1 shows a comparison of the EMBL-GB-deposited cDNA sequence of the SH2 domain of human STAT (SEQ ID NO:3) with the corresponding human HepG2 (nucleotides 1689–2112 of SEQ ID NO:1) and mouse liver (SEQ ID NO:5) cDNA fragments. The shown 424 bp nucleotide sequence and its numbering are from the SH2 domain of the human STAT3 cDNA sequence deposited in the EMBL-GB databases (Akira et al., 1994). Nucleotides at variance identified in human HepG2 (this patent application) and mouse liver cDNAs (Akira et al., 1994) are reported above the full sequence, in bold and underlined. Also in bold and underlined on the full sequence is indicated the nucleotide change resulting in a variation at the amino acid level, a Leucine coded in the deposited sequence being substituted by a Valine in the new sequence of this patent application. Amino acid sequences encoded by the hEMDL and m liver cDNAs are SEQ ID NOS:4 and 6, respectively. Primers US0; LS0; US1; LS1; LS2; US3; LS3; US4 and LS4, used in RT-PCR reactions are indicated by bold arrowhead above the sequences.

The position of primers US0/LS0 in the hSTAT3 sequence is shown in FIG. 1.

Additional primers for isolating the entire human STAT 3 cDNA were: Primer STAU, Primer STAL, Primer STBU and Primer STBL.

Two additional primer pairs, called US1/LS1 and US1/LS2, amplifying products of 285 and 111 bp respectively, were uniquely specific for the original published sequence of human STAT3 cDNA (Akira et al., 1994), but not for the STAT3 variant sequence we have found in this patent application. At least one nucleotide at variance between the published and the variant STAT3 sequences was positioned at the 3' end of each primer.

The US3/LS3 pair of primers was uniquely specific for the variant hSTAT3 sequence described in this patent application. This US3/LS3 pair of primers did amplify a 111 bp fragment specifically in the hSTAT3 variant sequence, corresponding to the sequence amplified by the US1/LS2 primers in the original published hSTAT3 cDNA sequence.

A validation pair of primers, US4/LS4, to create an artificial hSTAT3 template of 285 bp corresponding to the expected product of primers US1/LS1, has been used.

RNA and RT-PCR

Total RNA from human HepG2 cells was prepared by the method of Birnboim (Birnboim, 1988). For other tissues and cells, RNA was extracted with the Trizol reagent available from Gibco, Grand Island, N.Y., USA, following manufacturer instructions.

Oligo(dT) was used to prime reverse transcription of 5 μg of total RNA with 200 U of SuperScript II reverse transcriptase (RT) in 50 μl reaction mixture. The RT reaction was carried out at 37° C. for 1 h and 30 min. Preparative PCR was then performed using the RT products as the cDNA templates. PCR reactions contained 10 μl of cDNA, 50 pmoles of each primer (see below), 2.5 units of Stratagene Pfu polymerase, 0.2 mM of each of the four deoxynucleotide triphosphates, 10 μl of Pfu buffer, in a reaction volume of 100 μl, overlaid with 50 μl of mineral oil.

Amplification was usually performed for 30 cycles with a temperature profile of 45 seconds at 94° C. (denaturation), 45 seconds at 50 to 60° C. (annealing) and 5 minutes at 72° C. (extention). PCR products were purified by centrifugation through Microcon 100 filters (Amicon) and then subjected to electrophoresis on 1.5% agarose gels in Tris/borate/EDTA buffer. Analytical PCRs were performed in capillary tubes, with the same concentration of reagents described above in ten-fold less volume, except for the Pfu polymerase which was substituted with 0.5 U of Taq polymerase. The temperature profile was 94° C. for denaturation, 55° C. for annealing and 72° C. for extension.

DNA sequencing

Figure 2A:
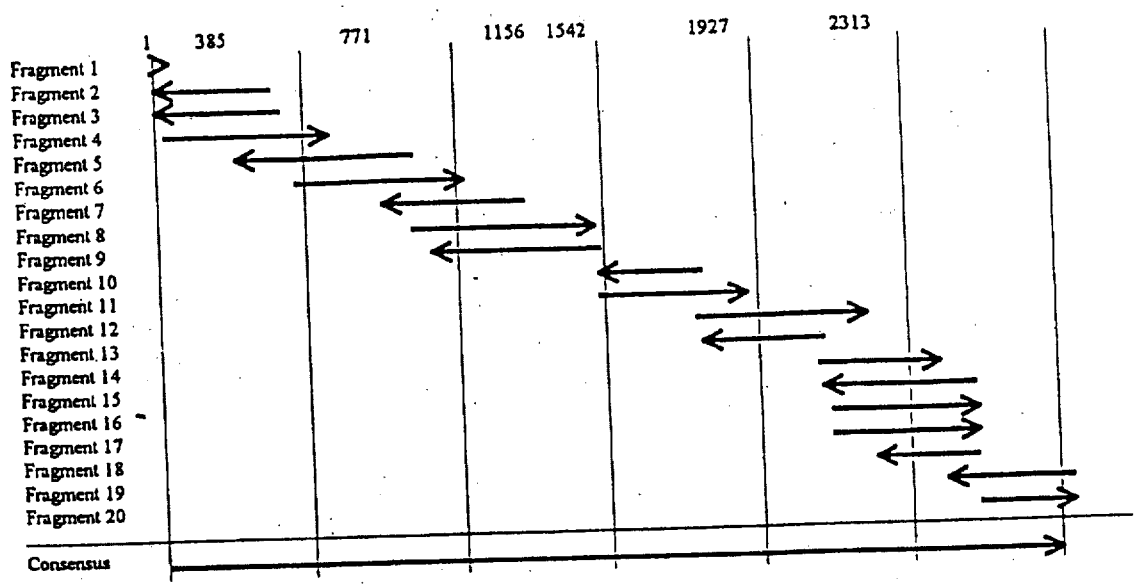
Figure 3A:
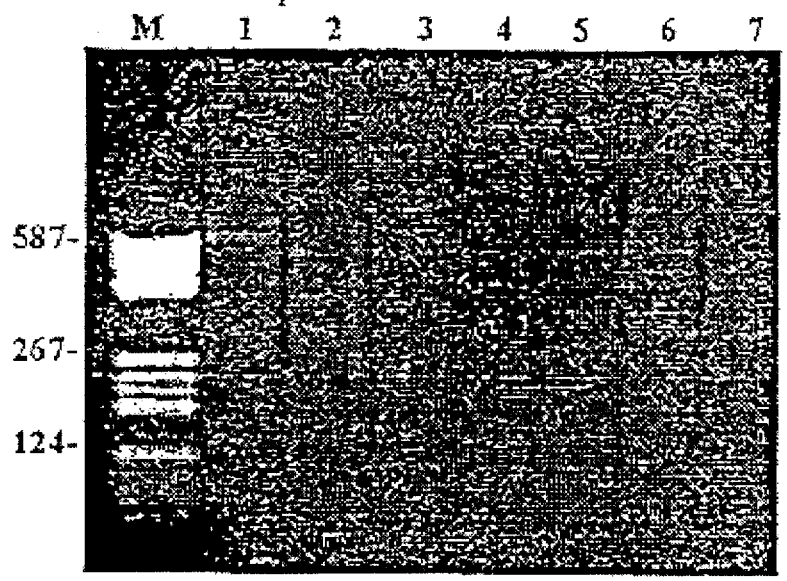
FIGS. 3A–3D show the analysis of the expression of the originally published hSTAT3 and the new variant hSTAT3 cDNAs. RNA was extracted with the Triozol regent, reverse-transcribed with oligo (dT) and the analytical PCR reaction was carried out with the TAG polymerase in capillary tubes, as described in the Examples.
Figure 3B:
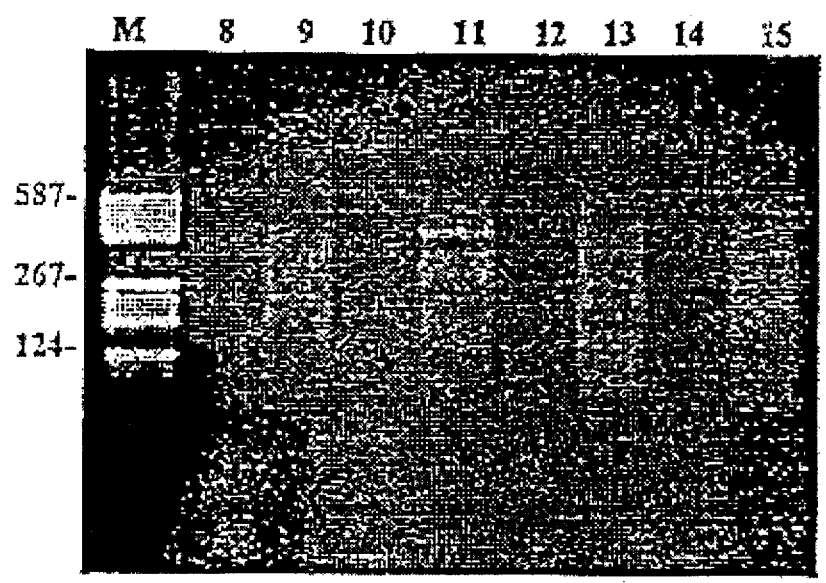
Figure 3C:
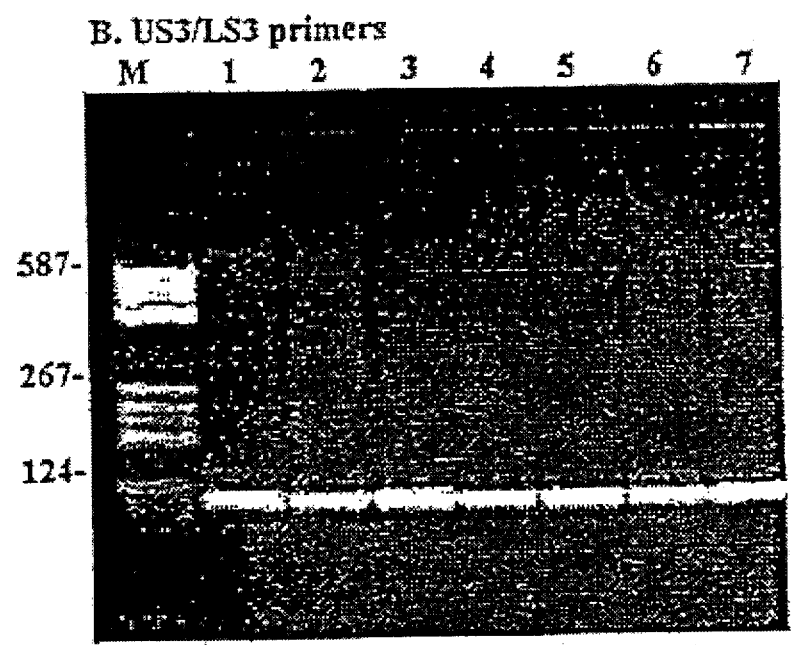
Figure 3D:

STAT3 PCR product were sequenced as depicted in FIG. 2. DNA sequences were performed with the dideoxy method, using a DNA sequencing kit (Perkin Elmer, Applied Biosystems Division, Foster City, Calif., USA) and an ABI model 373A automated sequence, following manufacturer instructions. The nucleotide sequences of all cDNA fragments were determined from sequencing both DNA strands. Nucleotide and deduced amino acid sequences were compared with those in GenBank and the Swiss-Prot database.

Results and discussion

Isolation and sequencing of a cDNA fragment coding for human STAT3

In order to isolate the SH2 domain of human STAT3, we have amplified by RT-PCR, a cDNA fragment of 424 base pairs corresponding to nucleotide positions between 1909 and 2332 of the published human placental STAT3 cDNA sequence (Akira et al., 1994), using total RNA from HepG2 cells.

This PCR fragment was then inserted in an expression vector, and the nucleotide sequence was determined. Results (FIG. 1) showed that 13 nucleotide residues differed from the original human placental cDNA sequence. The majority of the 13 modified residues were located in third colon position, resulting in no change of the corresponding amino acid sequence.

Only one mutated nucleotide residue resulted in the substitution of a leucine at position 667 in the human STAT3 protein with a valine (FIG. 1). We have then amplified from HepG2 cells two additional cDNA fragments corresponding to the whole coupling region of the human STAT3 cDNA. Sequencing of these fragments (FIG. 2) showed that overall 43 nucleotide were at variance with the publishing sequence, corresponding to a total of 6 amino acid changes (Akira et al., 1994).

The published human and mouse STAT3 consensus sequences are known to differ by 172 nucleotides, while the new human STAT3 sequence we present here differs by 193 residues with the mouse sequence (Raz et al., 1994; Akira et al., 1994; Zhong et al., 1994).

Thus, at the nucleotide level, the new human STAT3 sequence results in a slightly increased evolutionary distance with the mouse sequence. A region ranging between nucleotides 1680 and 1940 of the original human sequence showed a high nucleotide conservation between man and mouse. Such conversion is lost when the new human sequence presented in this patent application is considered.

On the contrary, at the amino acid level the new human sequence is more closely related to the mouse sequence. All six changes in the new human STAT3 amino acid sequence return the corresponding original mouse (and rat) residues, so that only one residue is now at variance between the human and the 770 amino acids consensus sequence of mouse STAT3: a glutamic acid at position 760 of the human sequence is substituted with an aspartic acid in the mouse sequence. The encoded STAT3 sequence therefore now results as one of the most conserved among known genetic determinants. As a reference, mouse and human STAT1 and STAT5 proteins differ by 67 and 29 amino acid residues, respectively.

STAT3, like other STAT family members, is known to bind several different proteins in order to accomplish its multiple functions (Darnell, 1997). The SH2 domain of STAT3 interacts with the intracellular portion of signal transducing receptor molecules, while the C-terminal region is important for activation and dimerization (Sasse et al., 1997), and the central region is important for DNA binding (Horvath et al., 1995).

Among the six amino acid changes described in the present patent application, one falls within the N-terminal region, at position 288. The second amino acid change falls at position 460, in the DNA-cloning domain. Two additional changes fall within the SH3 domain, at position 548 and 561 respectively.

Finally, two more amino acid changes fall within the SH2 domain at position 667 and in the C-terminal region, at position 730 respectively (See FIG. 2).

Characterization of the new STAT3 sequence variant

In order to determine the nature of the new sequence variant presented here, we have designed three pairs of primers with 3' ends corresponding to nucleotide positions at variance between the two human cDNA sequences. The first and the second pair of primers (US1/LS1 and US1/LS2) were exclusively specific for the original published nucleotide sequence of the hSTAT3 cDNA, while the third pair of primers (US3/LS3) was exclusively specific for the new variant human STAT3 nucleotide sequence we have determined.

We have used the two primer pairs US1/LS1 and US3/LS3 (specific for the original and the new variant sequences respectively) to amplify RNAs from 11 different human tissues in 22 separate RT-PCR reactions. Each RNA source we have examined was derived from pools of 1 to 17 individuals, with a total of 31 individuals analyzed.

Since the original hSTAT3 cDNA sequence was derived from human placenta, this tissue was included among the 11 RNA sources tested. As shown in FIG. 3, only the pair of primers specific for the new sequence variant were able to amplify all the eleven RNAs tested, resulting in the expected amplification product, while no significant band could be obtained in any RNA tested with the primers corresponding to the original published hSTAT3 sequence. Since the US1/LS1 primers did not result in any significant amplification product, we wanted to verify whether this failure was due to a defect in the printers, either in their intrinsic ability anneal to the appropriate template, or in their ability to prime the amplification reaction.

In other words, we wanted to validate the US1/LS1 pair of primers. Validation primers US4/LS4 were thus designed to match exactly primers US1/LS1, but each primer with a 3' extension matching the hSTAT3 variant sequence determined in this work.

Amplification would then result in an artificial hybrid template composed of the hSTAT3 variant sequence fragment, with its 5' and 3' ends identical to primers US1 and LS1 respectively. This artificial template should allow effective amplification with primers US1/LS1, even in the absence of the corresponding natural DNA template (i.e., the original, published hSTAT3 cDNA fragment of 285 bp).

Figure 4A:
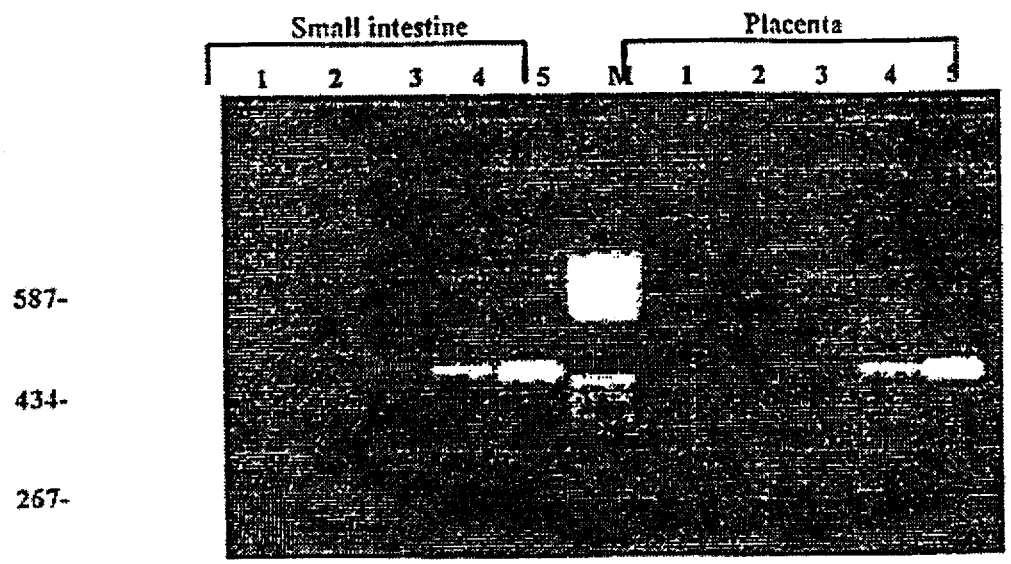
FIGS. 4A and 4B show the amplification of an artificial DNA template with primers US1/LS1. The artificial DNA template composed of the hSTAT3 variant sequence fragment flanked at its 5' end by the US1 primer sequence and at its 3' end by the LS1 primer sequence, was created by preparative PCR, using primers US4/LS4, from HepG2 cDNA (where only the variant sequence could be amplified, not shown), as described in the Materials and methods section. The artificial template was fractionated in 2% agarose gel and the relevant band of 285 bp was purified with the agarose gel DNA extraction kit (Boeringer Mannheim, Mannheim, Germany). This template was then spiked at various concentrations to 1 μl of the relevant cDNA (originated from approximately 100 ng of the corresponding RNA). Lanes: M) Molecular size markers. 1) No spiking. 2) 0.3 fg of artificial template spiked. 3) 3 fg of artificial template spiked. 4) 30 fg of artificial template spiked. 5) 300 fg of artificial template spiked.
Figure 4B:
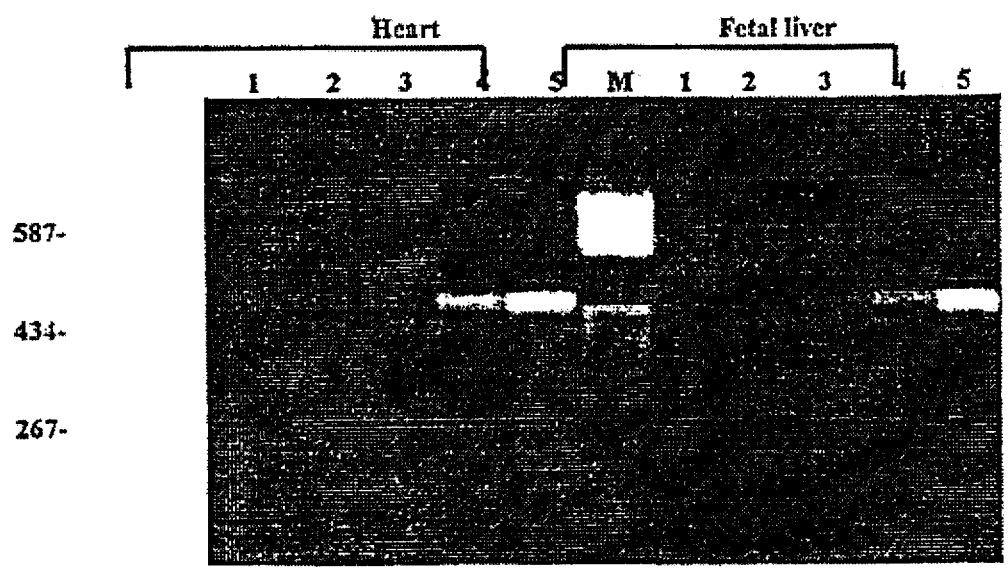

This artificial temple was obtained by PCR with primers US4/LS4, and spiked at different concentrations in human placental cDNA and in other human cDNAs. Primers US1/LS1 were then used to amplify these spiked cDNAs, and a PCR product of the expected size was readily obtained (FIG. 4). This result therefore excluded a failure of the US1/LS1 pair of primers in the amplication reaction.

Figure 5:
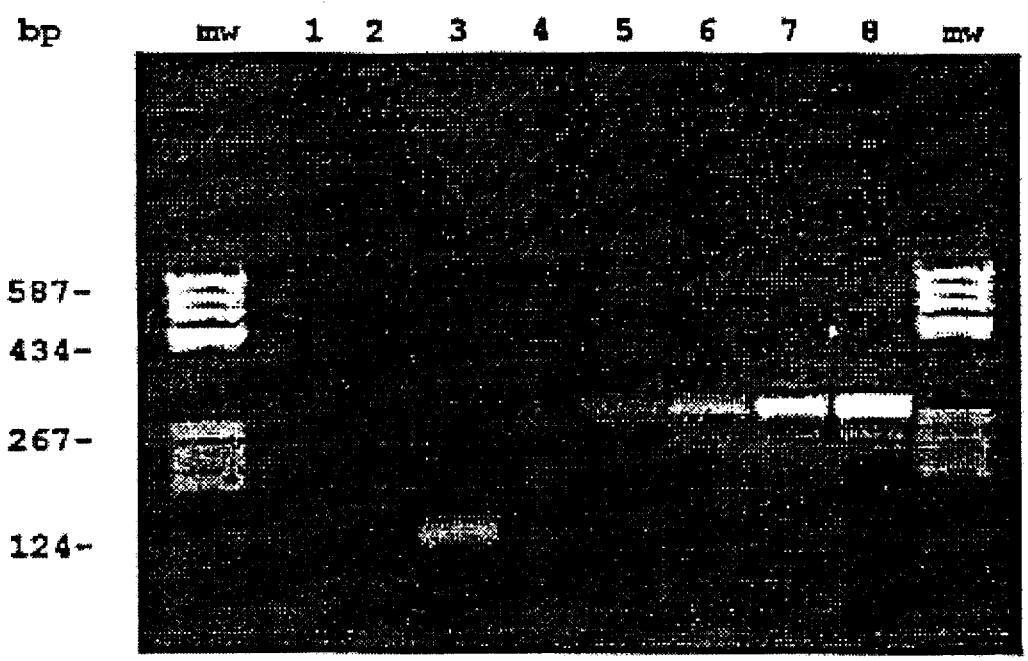
FIG. 5 shows the PCR analysis of the original hSTAT3 and the new variant hSTAT3 genomic sequence fragment. 40 ng of human genomic DNA were used in analytical PCR reactions carried out in capillary tubes, as described in the Materials and methods section. Lanes: M) Molecular size markers, 2, 4) Genomic DNA amplified with the US1/LS1 pair of primers, specific for the original, published hSTAT3 sequence. 2) Genomic DNA amplified with the US1/LS2 pair of primers, specific for the original published hSTAT3 sequence. 3) Genomic DNA amplified with the US3/LS3 pair of primers specific for the new variant hSTAT3 sequence. 5, 6, 7, 8) Genomic DNA amplified with the US1/LS1 pair of primers and spiked with 0.3, 3, 30 and 300 fg respectively, of the US4/LS4-amplified artificial DNA template.

We have then used the US1/LS1, US1/LS2 and US3/LS3 pairs of primers to amplify human genomic DNA. The expected amplication product was again obtained only with the primer pair specific for the new variant sequence we have determined (FIG. 5).

We have shown that the mouse and the revised human STAT3 protein sequences are highly conversed, with only one residue being at variance between the two species over 770 amino acid residues of total length.

We could not detect the hSTAT3 nucleotide sequence originally described by Akira et al. (Akira et al., 1994) in any of the human genomic or cDNA sources we have tested. The original published nucleotide sequence and the new sequence variant are not therefore different genes or splice variants contemporaneously present in the same genome, since only one sequence (the one identified in this patent application) was detected in each human nucleic acid source tested. The two hSTAT3 sequence variants could be different alleles.

In this case however, the new variant sequence is likely to be predominant, since it was represented in all nucleic acid samples tested, derived from a total of 31 individuals. The original published hSTAT3 sequence was not represented at all in these individuals.

References

1. Akira, S., et al., (1994) Cell 77, 63–71;
2. Azam, M., et al., (1995) EMBO Journal 14, 1402–1411;
3. Birnboim, H. C. (1988) Nucleic Acids Research 16, 1487–1497;
4. Darnell, J. E. (1997) Science 277, 1630–1635;
5. Gouilleux, F., et al., (1995) EMBO Journal 14, 2005–2013;
6. Gram, H., et al., (1992) Proceedings of the National Academy of Sciences of the United States of America 89, 3576–3580;
7. Harroch, S., et al., (1994) Journal of Biological Chemistry 269, 26191–26195;
8. Hemmann, U., et al., (1996) Journal of Biological Chemistry 271, 12999–13007;
9. Horvath, C. M. et al., (1995) Genes & Development 9, 984–994;
10. Iwatsuki, K., et al., (1997) J. Biol. Chem. 272, 8149–8152;
11. Kapetein, A., et al., (1996) Journal of Biological Chemistry 271, 5961–5964;
12. May, P., et al., (1996) FEBS Lett. 394, 221–226;
13. Minami, M., et al., (1996) Proceedings of the National Academy of Sciences of the United States of America 93, 3963–3966;
14. Quelle, F. W., et al., (1995) Molecular & Cellular Biology 15, 3336–3343;
15. Raz, R., et al., (1994) Journal of Biological Chemistry 269, 24391–24395;
16. Sasse J. et al., (1997) Mol. Cell Biol. 17, 4677–4686;
17. Seidel, H. M., et al., (1995) Proceedings of the National Academy of Sciences of the United States of America 92, 3041–3045;
18. Shi, W., et al., (1996) International Immunology 8, 1205–1211;
19. Silva, C. M., et al., (1996) Molecular Endocrinology 10, 508–518;

20. Stahl, N., et al., (1994) Science 263, 92–95;
21. Stahl, N., et al., (1995) Science 267, 1349–1353;
22. Tian, S. S., et al., (1994) Blood 84, 1760–1764;
23. Wegenka, U. M., et al., (1993) Mol. Cell Biol. 13, 276–288;
24. Wegenka, U. M., et al., (1994) Molecular & Cellular Biology 14, 3186–3196;
25. Yamanaka, Y. et al., (1996) EMBO Journal 15, 1557–1565;
26. Zhang, D., et al., (1996) Journal of Biological Chemistry 271, 9503–9509.
27. Zhong, Z., et al., (1994) Science 264, 95–98.

What is claimed is:

1. A human STAT3 protein, comprising the amino acid sequence of SEQ ID NO:2, or a functionally equivalent salt, or a fusion protein thereof.

2. A composition, comprising the protein of claim 1 and a carrier or excipient.

* * * * *